United States Patent [19]

Mattsson et al.

[11] 4,453,075

[45] Jun. 5, 1984

[54] METHOD FOR LOCALIZING A REGION IN THE HUMAN BODY, IN PARTICULAR VENOUS THROMBI, BY THE UPTAKE OF A RADIOACTIVE SUBSTANCE, PARTICULARLY $^{125}$I-FIBRINOGEN

[76] Inventors: Sören Mattsson, Persikevägen 43, S-223 55 Lund; Nils-Gunnar Holmer, Gilleskroken 7, S-222 47 Lund; Kurt Bernstein, Näktergalsvägen 26, S-230 50 Bjärred; Ulf Ulmsten, Geijersgatan 39, S-216 18 Malmö; Birger Astedt, Bokgatan 11, S-230 40 Bara; Lars Jacobsson, Aspnäsvägen 96, S-582 62 Linköping, all of Sweden

[21] Appl. No.: 481,977

[22] Filed: Apr. 4, 1983

Related U.S. Application Data

[62] Division of Ser. No. 195,964, Oct. 10, 1980.

[30] Foreign Application Priority Data

Oct. 17, 1979 [SE] Sweden .................. 7908576-7

[51] Int. Cl.³ .............................................. G01T 1/20
[52] U.S. Cl. ............................................... 250/363 S
[58] Field of Search .................. 250/302, 303, 363 R, 250/363 S, 369; 128/1.1, 653

[56] References Cited

U.S. PATENT DOCUMENTS

| 3,409,774 | 11/1968 | Dykeman | 250/252.1 |
| 3,812,245 | 5/1974 | Dugan | 250/303 |
| 4,016,418 | 4/1977 | Horrocks et al. | 250/303 |

Primary Examiner—Janice A. Howell
Attorney, Agent, or Firm—Edwin E. Greigg

[57] ABSTRACT

An apparatus for determining the depth position of venous thrombi in the lower extremities utilizes a unique property in $^{125}$I. This resides in the fact that in approximately half of all disintegrations, two photons are emitted simultaneously. These two coincident photons have, like separately emitted photons, an energy of approximately 28 keV. A scintillation detector perceives the coincidently emitted photons as one photon of an energy of 56 keV. The quotient between the number of separately emitted photons and the number of coincident photons may thus be determined. This quotient constitutes a parameter which is greatly dependent on the distance between the detector and the source of radiation, whereby there is obtained a possibility of determining the depth of the thrombus.

6 Claims, 4 Drawing Figures

METHOD FOR LOCALIZING A REGION IN THE HUMAN BODY, IN PARTICULAR VENOUS THROMBI, BY THE UPTAKE OF A RADIOACTIVE SUBSTANCE, PARTICULARLY $^{125}$I-FIBRINOGEN

This is a division of application Ser. No. 195,964 filed Oct. 10, 1980.

The present invention relates to an apparatus for localizing a region in the human body by the detection of a compound marked with a radioactive substance, in particular $^{125}$I-fibrinogen, by means of a detector for disintegration radiation from the detected region.

The risk of blood clots (thrombi) after certain surgical operations requires, in many cases, a careful watch over the patient such that diagnosis can be made at an early stage. Thrombi in deep veins are of particular interest, since these thrombi (as opposed to thrombi in the superficial veins) are particularly dangerous in that they can, during their growth, destroy the blood circulation in the extremity, possibly become loose and terminate, via the blood circulation, in the lungs with perilous if not fatal results. It is, therefore, vital that therapeutic measures be applied as soon as possible. Since the therapy in question may involve side-effects, it should, however, only be employed in cases of real need, for example it should not be applied if the patient is suffering only from superficial thrombi.

Forms of X-ray examination using contrast medium have been used for determining the presence and position of thrombi. However, these methods possess disadvantages in that they are relatively circumstancial and expensive and may also be painful to, not to say dangerous for the patient. Hence, it is not entirely inconceivable that such an examination as phlebography itself may give rise to thrombosis.

An alternative method for determining the presence and position of thrombi is the so-called $^{125}$I-fibrinogen detection test which is regularly used for the diagnosis of venous thrombi in the leg. The method is based on the administration of $^{125}$I-fibrinogen (the fibrin of the blood) which, on coagulation, accumulates as fibrin filaments in the thrombus. The thereby increased activity may be monitored exteriorly by means of a detector which is sensitive to the decay radiation from the $^{125}$I-fibrinogen, such as a scintillation detector. The disadvantage inherent in this method is that it cannot distinguish between thrombi in superficial veins and thrombi in deep veins, that is to say it allows only for determination of the position of a thrombus calculated from the surface of the body, and not the depth location of the thrombus.

In comparison with phlebography, the $^{125}$I-fibrinogen uptake test gives roughly 20% "false positive" findings on examination of thrombi in the leg, and it is probable that this difference may be related to the presence of thrombi in the superficial veins.

The object of the present invention is to realize an examination apparatus which unites the advantages of the above-described methods, that is to say the accuracy of positional determination of phlebography and the bloodlessness, safety and simplicity of the $^{125}$I-fibrinogen test, this being achieved without involving the disadvantages of either method.

This object is attained in an apparatus of the type disclosed by way of introduction, the apparatus being, to this end, characterized by a discriminator device connected to a detector for distinguishing between disintegrations which give rise to the emission of non-coincident photons of an energy within a first interval, and disintegrations which give rise to the emission of substantially coincident photons having a total energy in a second interval substantially separate from the first interval, and means, connected to the discriminator device, for counting the number of disintegrations of each type and for calculating the distance from the detector to the source region from the relationship between the two numbers.

The invention employs a unique property in the characteristic of the decay of $^{125}$I. This isotope decays via electron capture to an excited level in $^{125}$Te. In this transition, on average 0.74 K X-rays per disintegration are emitted. Deexcitation of the excited level occurs substantially by internal conversion which, on average, gives 0.67 K X-rays per disintegration. A minor portion (7%) of the deexcitation occurs via $\gamma$ emission. The energy of the X-rays varies from 27 keV to 31 keV with a weighted mean value of 28 keV.

In approximately half of these integrations, a photon is emitted both during electron capture and in deexcitation. The mean number of such events per disintegration is given by the product 0.74·(0.67+0.07), approximately equal to 0.54. Two X-ray photons or one X-ray and one $\gamma$ photon are then emitted almost simultaneously with no direction correlation.

The probability of detecting both the coincident photons depends, int. al., upon the size of the detector employed, the distance between the detector and the region having the radioactive isotope, and the attenuation of the material between the detector and the region. A similar dependency relates to the probability of total detection of both the coincident and non-coincident photons. The quotient between the number of coincident registrations, $N_c$, and the total number of photons registered $N_t$, can, particularly in view of the fact that the emitted radiation is relatively monochromatic in the case of $^{125}$I, be shown to be of the type:

$$N_c/N_t = K_a \cdot \Omega/4\pi \cdot e^{-\mu d} \cdot \epsilon$$

wherein $K_a$ is a constant, $\Omega$ is the solid angle under which the detector is seen from a point source for the radiation, $\mu$ is the effective attenuation coefficient of the interjacent material which is material-and energy-dependent, d is the distance between the radiation source and the detector, and $\epsilon$ is the efficiency of the detector.

In the above expression, $N_t = N_n + 2N_c$, wherein $N_n$ is the number of detected non-coincident photons.

For practical measurements, an experimental determination is required of the relationship between the distance d and the quotient $N_c/N_t$. It then proves that the distance d may be described by means of an expression of the type: $d = k_1 \cdot \ln(k_2 + N_t/N_c)$, wherein $k_1$ and $k_2$ are constants.

As a result of use of the apparatus according to the invention, it is also possible to determine the depth location of a thrombus, whereby the above-disclosed object is attained.

Thus, the property which is utilized in the decay characteristic for the isotope $^{125}$I is the presence of substantially coincidently emitted photons in a certain zone of the disintegration, these coincident photons being separately detectable, that is to say have a total energy which lies within an energy interval in which no individual photons are emitted. Other radioactive isotopes than $^{125}$I may, naturally, possess this property, but $^{125}$I is the isotope which at present is to be preferred.

The nature of the present invention and its aspects will be more readily understood from the following brief description of the accompanying drawings, and discussion relating thereto.

Figure 1:
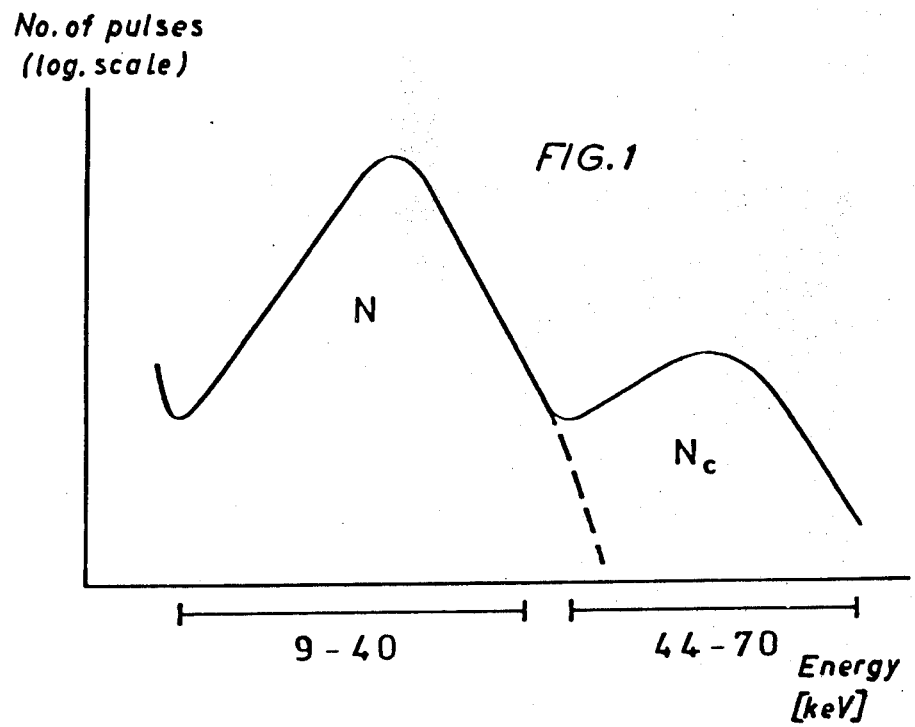
FIG. 1 shows the energy distribution of the photons emitted from a source of $^{125}$I.

The diagram in FIG. 1 shows the energy distribution of photons emitted from the $^{125}$I-radiation source, these having been detected by means of a thallium activated sodium iodide detector. Such a scintillation detector may, for example, have a scintillation crystal with a diameter of 124 mm and a thickness of 1.5 mm as well as being provided with a brass collimator having a length of 50 mm, an opening diameter of 40 mm and a thickness of 5 mm. The distribution curve has one peak at approximately 28 keV, a peak which may be related to individually detected photons, and one peak at approximately 56 keV, a peak which may be related to pairwise coincidently detected photons which are registered by the detector as a single photon of an energy in the region about 56 keV.

Figure 2:
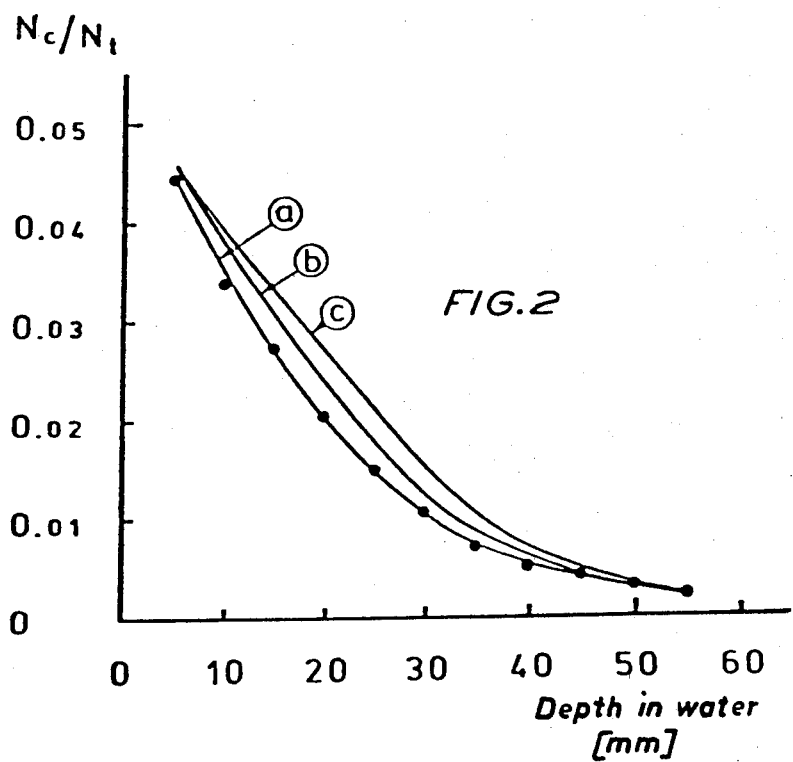
FIG. 2 shows experimentally derived relationships between the depth in water of a radiation source and the quotient $N_c/N_t$.

As was pointed out earlier, experimental determination of the relationship between, on the one hand, the ratio between the number ($N_c$) of detected photons of an energy at about 56 keV and the total number ($N_t$) of detected photons, and, on the other hand, the distance between the radiation detector and the source of radiation is to be preferred. Examples of this relationship are shown in FIG. 2 which illustrates how the quotient $N_c/N_t$ varies with the distance between a radiation detector and a punctiform (curve a) or linear (curves b and c) radiation source which is immersed in water, the attenuation coefficient of water substantially corresponding to the attenuation coefficient of the muscle tissue of the body.

Figure 3:
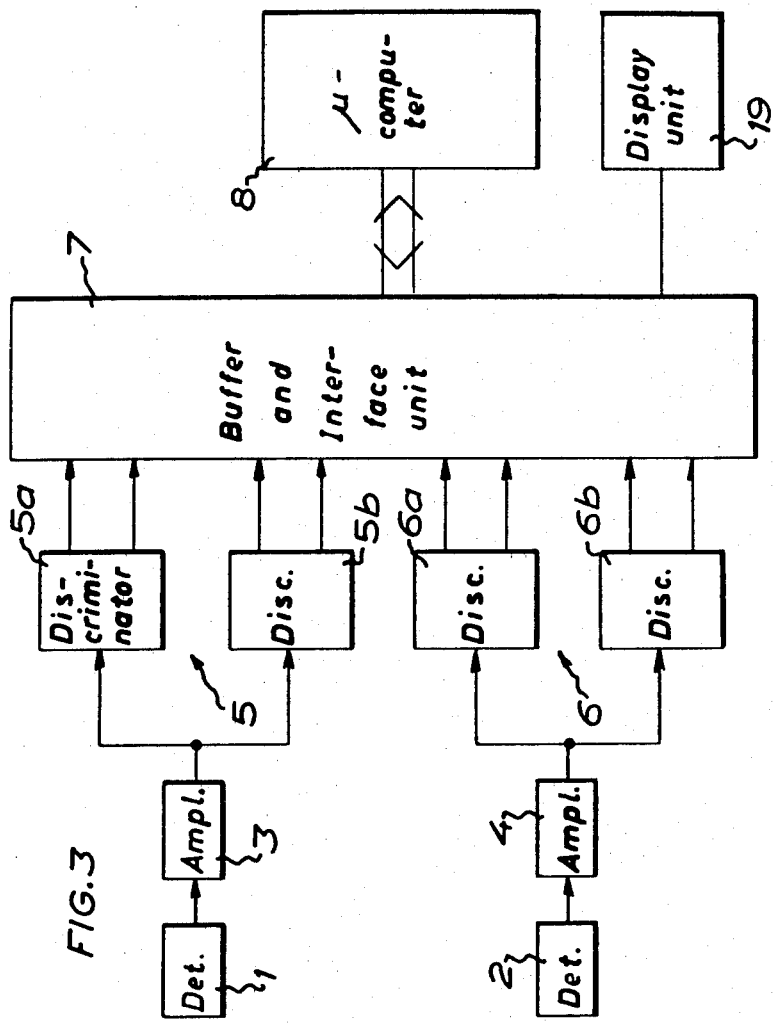
FIG. 3 is a block diagram of one embodiment of the apparatus according to the invention.

The embodiment of the apparatus according to the invention shown in FIG. 3 comprises two radiation detectors 1 and 2 which may be scintillation detectors of the above-described type combined with photomultipliers which, in a known manner, give an output pulse for each detected photon or detected pair of coincident photons, this output pulse being of an amplitude which is substantially proportional to the energy of the photon or pair of coincident photons, respectively. The output pulses of each detector 1, 2 are amplified by amplifiers 3 and 4 and are thereafter fed to discriminators 5 and 6 which may each consist of two single-channel analyzers 5a and 5b, and 6a and 6b, respectively. Since the apparatus is to be utilized for registering uptake of a compound marked with $^{125}$I, the analyzers 5a and 6a are set so as to react to photons of an energy within an interval (a so-called window) about the value 28 keV, whereas the corresponding value for the analyzers 5b and 6b is approximately 56 keV. Pulses emitted from the analyzers 5a, 6a, 5b and 6b whose number agrees with the number of registrations in each respective window are impressed on corresponding buffer circuits in a buffer and interface unit 7 to and from which unit information transfer can be effected respectively from and to a microcomputer 8.

Figure 4:
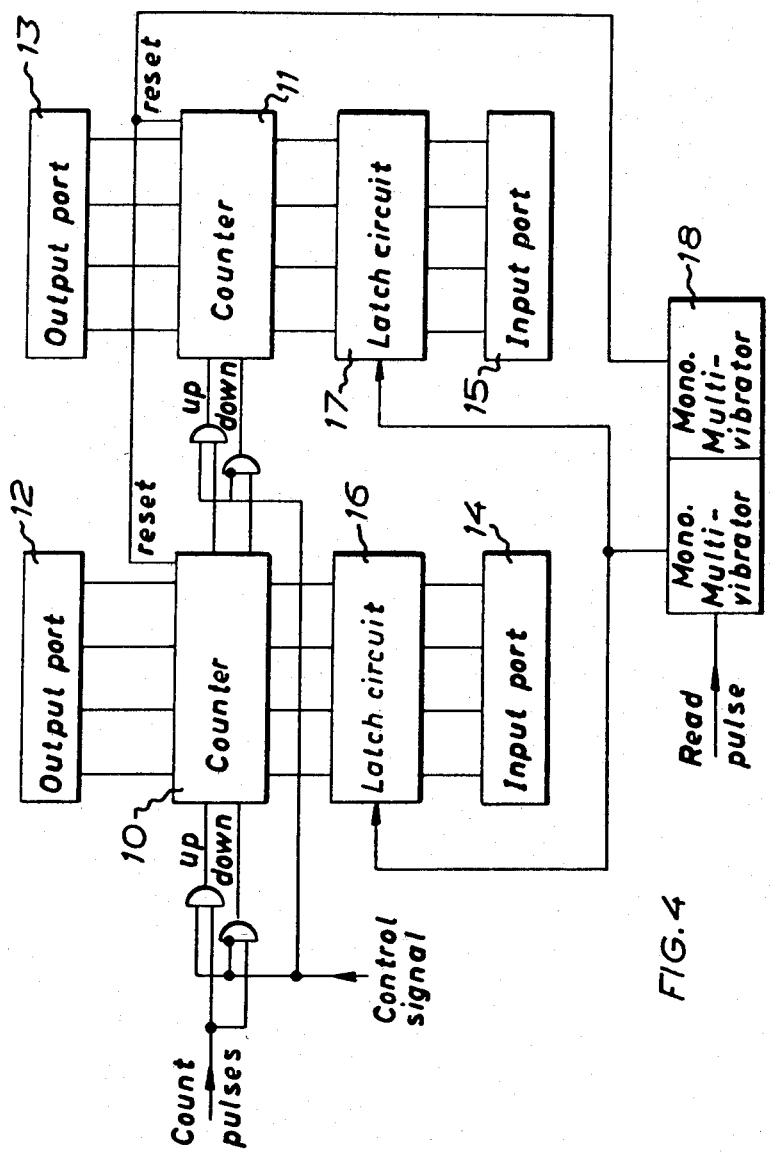
FIG. 4 shows a number of the buffer circuits included in the apparatus according to the embodiment of FIG. 3.

The above-described buffer and interface unit 7 may, for each single-channel analyzer output, be provided with a buffer circuit of the type shown in FIG. 4. More precisely, this circuit includes two binary counters 10, 11 (e.g. of the 74LS193 type), which count the pulses occurring on each respective single-channel analyzer output, a control signal from the computer 8 determining whether counting is to be effected upwardly or downwardly. The counters 10 and 11 are, on one side, connected to two output ports 12, 13 from the computer 8 and, on the other side, are coupled to two input ports 14, 15 to the computer each by the intermediary of their latch circuits 16 and 17 (for example of the 74LS175 type). Feed out of the contents of the counters 10 and 11 to the latch circuits 16 and 17 and thence to the input ports 14 and 15 of the computer 8 is realized by means of a read-out pulse from the computer 8, this readout pulse being supplied to a multivibrator circuit 18 (e.g. of the 74L221 type) having two monostable multivibrators, whereby the contents of the counters 10 and 11 are first transmitted to the latch circuits 16 and 17 and the counters 10 and 11 are thereafter zeroized.

The use of the above-described apparatus in conjunction with the determination of the location of venous thrombi in a leg will be described below. By way of preparation, $^{125}$I-fibrinogen was injected into the patient. The detectors 1 and 2 were thereafter placed, for example, over the heart, whereafter the single-channel analyzers were set with respect to the center of each respective window in such a manner that maximum sensitivity is attained in each channel. For establishing a norm of subsequently measured values, a measurement is thereafter carried out on the heart, which gives a reference for radiation activity. Thereafter, the site of the thrombus along the leg is established, which may be effected manually, mechanically or electrically under control from the computer 8. On manual location of the site of the thrombus, the detector 1 is, for example, moved along the leg and the activity along the leg is monitored. A maximum value of a thus obtained activity curve discloses the position of a venous thrombus. Mechanically, location of the site of the thrombus may be effected by mounting a detector on, for example, a lead screw which, under control from the computer, is caused to move the detector along the length of the leg, the activity being monitored in a manner corresponding to that in the manual examination. The site of the thrombus along the leg may also be determined purely electrically in that a plurality of detectors is disposed along the leg, the activities monitored by the different detectors being utilized by the computer for determining the position along the leg where the thrombus is to be found.

When the site of the thrombus has been determined, the detector 1 is placed in a suitable position over the thrombus, whereas the detector 2 is placed on a corresponding site on the other leg of the patient for detecting background radiation, which is not necessary in the first examination for determining the site of the thrombus along the leg. Thereafter registration is commenced and is terminated after a predetermined time or once a predetermined number of coincident photons has been counted, or, finally, once the depth position of the thrombus can be determined with a predetermined level of accuracy. Combinations of these conditions may also be utilized for terminating the registration.

On registration for a predetermined period of time, the number of pulses registered in the counters 10 and 11 and in the corresponding counter are periodically transmitted, that is to say at an interval of 100 ms, to the computer 8 via the latch circuits 16 and 17 and the input ports 14 and 15. On registration of a predetermined number of photons, a suitable number can be set in the counters 10 and 11 via the output ports 12 and 13 of the computer 8, whereafter the counters 10 and 11 are caused, by means of a control signal from the computer 8, to count down on receipt of pulses from each respective detector.

The buffer circuits described above and shown in FIG. 4 are necessary when, for example, a computer of the ABC80 type is used and when the program is written in BASIC[1]) If the program is instead written in assembly language, the computer may be caused to operate so rapidly that no buffer circuits are required.

Thus, as a modification of the apparatus shown in FIG. 3, the buffer circuits in the unit 7 may be dispensed with. As a further modification, an analog-digital converter may be coupled in, instead of the single-channel analyzers, or be coupled in parallel with these analyzers. An analog-digital conversion of the amplitude of the pulses from, for example, the amplifier 3 makes possible the retrieval of a spectral distribution of the registered photons. When an analog-digital converter is used instead of the single-channel analyzers, each analog-digital converter replaces two single-channel analyzers. For collection of data in this manner, it is necessary that the microcomputer be programmed in assembly language such that sufficient rapidity be attained. Moreover, it is required that the analog-digital converter be of sufficient capacity, that is to say a capacity of from 10 to 12 bits, and at the same time have a shorter conversion time (100 μs) than the corresponding most rapid coincidence (1) Beginner's Allpurpose Symbolic Instruction Code time (approximately 1 ms). The display unit 19 of the computer may be used for presenting the distribution curve whose appearance may progressively be updated.

As was mentioned earlier, the above-described apparatus may in one embodiment have a plurality of detectors placed along the leg in question. In this case, the microcomputer commences its examination first by reading in, via the buffer and interface unit, the count pulses emanating from each respective detector. Thereafter, the microcomputer determines under which detector a possible thrombus may be located and makes, thus, an accurate collection of data, thereafter calculating the depth of the thrombus. If the thrombus is located between two detectors, a measurement is effected with both of these detectors and the actual position of the thrombus is thereafter calculated, as well as its distance from the skin.

We claim:

1. A method for localizing the depth of a region in the human body by the detection of a compound marked with a radioactive substance by means of a detector device for perceiving disintegration radiation from the region, comprising the steps of distinguishing between disintegrations of a first type which give rise to substantially non-coincident photons of an energy in a first interval and disintegrations of a second type which give rise to the mission of substantially coincident photons of a total energy in a second interval substantially separate from said first interval, counting the number of disintegrations of each of said types, and calculating the distance from the detector to the region from the empirical formula:

$$d = k_1 \cdot \ln(k_2 + N_t/N_c)$$

where $d$ = the distance from the detector device to said region $N_t$ = the total number of detected disintegrations $N_c$ = the number of detected disintegrations of the second type $\ln$ = the natural logarithm; and $k_1$ and $k_2$ are experimentally determined constants.

2. A method for localizing the depth of a region in the human body according to claim 1, including the steps of injecting into the human body a radioactive substance comprising $^{125}I$ and utilizing a detector device configured to provide an energy of a first interval centered about 28 keV and a second interval centered about approximately 56 keV.

3. A method for localizing the depth of a region in the human body according to claim 1, including the step of counting the disintegration radiations from the region and the step of simultaneously registering the disintegration radiations from a reference region for determining background radiation.

4. A method for localizing the depth of a region in the human body according to claim 2, including the step of counting the disintegration radiations from the region and the step of simultaneously registering the disintegration radiations from the reference region for determining background radiation.

5. A method for localizing the depth of a region in the human body according to claim 1, including the step of counting the number of disintegrations from a plurality of regions of the human body in order, prior to detection of coincident and non-coincident photons, to determine the region of highest activity.

6. A method for localizing the depth of a region in the human body according to claim 2, including the step of counting the number of disintegrations from a plurality of regions of the human body in order, prior to detection of coincident and non-coincident photons to determine the region of highest activity.

* * * * *